(12) United States Patent
Kim et al.

(10) Patent No.: US 11,224,629 B2
(45) Date of Patent: Jan. 18, 2022

(54) FRACTION OF MELISSA LEAF EXTRACT HAVING ANGIOGENESIS AND MMP INHIBITORY ACTIVITIES, AND COMPOSITION COMPRISING THE SAME

(71) Applicant: ANGIOLAB, INC., Yuseong-Gu Daejeon (KR)

(72) Inventors: Min-Young Kim, Daejeon (KR); Jong Cheon Hahm, Daejeon (KR); Byung Young Park, Daejeon (KR); Eun Kyu Park, Kyounggi-do (KR); Hee Suk Lee, Seoul (KR)

(73) Assignee: ANGIOLAB, INC., Daejeon (KR)

( * ) Notice: Subject to any disclaimer, the term of this patent is extended or adjusted under 35 U.S.C. 154(b) by 0 days.

(21) Appl. No.: 17/084,978

(22) Filed: Oct. 30, 2020

(65) Prior Publication Data

US 2021/0052686 A1 Feb. 25, 2021

Related U.S. Application Data

(60) Division of application No. 12/609,516, filed on Oct. 30, 2009, now Pat. No. 10,894,071, which is a continuation-in-part of application No. PCT/KR2008/004938, filed on Aug. 25, 2008.

(30) Foreign Application Priority Data

Aug. 23, 2007 (KR) .......................... 10-2007-0084929

(51) Int. Cl.
*A61K 36/53* (2006.01)

(52) U.S. Cl.
CPC .................................... *A61K 36/53* (2013.01)

(58) Field of Classification Search
None
See application file for complete search history.

(56) References Cited

U.S. PATENT DOCUMENTS

| | | | |
|---|---|---|---|
| 6,569,468 B2 | 5/2003 | Xiao | |
| 9,155,773 B2 | 10/2015 | Kim | |
| 2004/0009244 A1 | 1/2004 | Kim et al. | |

FOREIGN PATENT DOCUMENTS

| | | |
|---|---|---|
| CA | 2629529 A1 | 5/2006 |
| CN | 1142338 A | 2/1997 |
| DE | 2952114 C2 | 1/1984 |
| EP | 0034214 A2 | 8/1981 |
| JP | 11-12270 A | 1/1999 |
| JP | 2008-520588 | 6/2008 |
| KR | 100473688 B1 | 3/2005 |
| KR | 100500298 B1 | 7/2005 |
| KR | 100645385 B1 | 11/2006 |
| WO | 2002/047701 A1 | 6/2002 |
| WO | 2007/040377 A1 | 4/2007 |
| WO | 2009/025532 A2 | 2/2009 |

OTHER PUBLICATIONS

Yanishlieva Nedjalka V et al: "Antioxidant activity of selected species of the family Lamiaceae grown in Bulgaria", Nahrung, vol. 39, No. 5-6, 1995, pp. 458-464, XP9153503, ISSN: 0027-769X (7 pages).

Brendler Thornas et al: "Lemon balm (*Melissa officinalis* L.): An evidence-based systematic review by the natural standard research collaboration", Journal of Herbal Pharmacotherapy, vol. 5, No. 4, 2005, pp. 71-114, XP9153568, ISSN: 1522-8940 (45 pages).

Jasna Canadanovic-Brunet et al: "Radical Scavenging, Antibacterial, and Antiproliferative Activities of *Melissa officinalis* L. Extracts", Journal of Medicinal Food, vol. 11, No. 1, Mar. 1, 2008 (Mar. 1, 2008), pp. 133-143, XP55010657, ISSN: 1096-620X, DOI: 10.1089/jmf.2007.580 (11 pages).

Ostman, ed. Treating and Preventing Obesity (2004), Wiley-VCH Verlag GmbH & Co. KgaA, Weinheim. "Summary" pp. 1-14.

Agata et al., "Melitric Acids A and B, New Trimeric Caffeic Acid Derivatives from Melissa officinalis", Chem. Pharm. Bull. 41(9) 1608-1611 (1993), 4 pages.

Kim et al., "Screening of Anti-angiogenic Activity from Plant Extracts", Korean Journal of Pharmacognosy 37(4): 253-257 (2006), 6 pages.

Written Opinion of the International Searching Authority for International Application No. PCT/KR2008/004938, dated Feb. 23, 2009, 4 pages.

*Primary Examiner* — Susan Hoffman
(74) *Attorney, Agent, or Firm* — FisherBroyles, LLP

(57) ABSTRACT

The present application describes an ethyl acetate fraction of *Melissa* leaf having excellent angiogenesis and MMP inhibitory activities, and a composition comprising the same.

2 Claims, 5 Drawing Sheets

Control

ALS-L1023

T1: low dose group
T2: medium dose group
T3: high dose group

FRACTION OF MELISSA LEAF EXTRACT HAVING ANGIOGENESIS AND MMP INHIBITORY ACTIVITIES, AND COMPOSITION COMPRISING THE SAME

CROSS-REFERENCE TO RELATED APPLICATIONS

The present application is a divisional of U.S. application Ser. No. 12/609,516, filed Oct. 30, 2009, now U.S. Pat. No. 10,894,071, which is a continuation-in-part of PCT/KR2008/004938, filed Aug. 25, 2008, the contents of each are incorporated by reference herein in their entirety.

BACKGROUND OF THE INVENTION

1. Field of the Invention

The present invention relates to an ethyl acetate fraction of Melissa leaf having excellent angiogenesis and MMP inhibitory activities, and a composition comprising the same. In particular, the ethyl acetate fraction of Melissa leaf is characterized in that Melissa leaf is extracted with 50~100% $C_1$~$C_6$ alcohol, and concentrated, and then the concentrated alcohol extract is suspended in water, and fractionated with ethyl acetate, and dried to obtain the ethyl acetate fraction of Melissa leaf.

2. General Background and State of the Art

Melissa (Melissa officinalis), a perennial herb in a Labiatae family, is also called lemon balm, balm, or dropsy plant as common and folk names.

Key constituents of the Melissa officinalis are flavonoids, terpene acids, volatile oils, glycosides of the alcoholic and phenolic compounds and caffeic acid derivatives. Especially, cynaroside, cosmosin, rhamnocitrin and isoquercitrin are abundant components as flavonoids, and ursolic acid is a component as terpene acid. Rosmarinic acid as caffeic acid derivatives is the most abundant component (about 4.7%), and geranial, neral, citronellal and eugenol are well known components as volatile oils contained in Melissa leaf extract.

Rosmarinic acid, an abundant non-volatile component of Melissa leaf extract, has strong anti-inflammatory and antipyretic effect, and essential oils have been used for depression, neurogenic headache, reducing memory, neuralgia, fever and also well known to have sedative, antibacterial, antiviral, antioxidant and antihormonal effects. Recently, Melissa leaf extract has included in blood circulation activator, which helps dilatation of peripheral blood vessels.

Angiogenesis is the process of generating new capillary blood vessels. Neovascularization is tightly regulated, and occurs during embryonic development, tissue remodeling, wound healing and periodic cycles of corpus luteum development (Folkman and Cotran, Relation of vascular proliferation to tumor growth, Int Rev Exp Pathol 16 207-248, 1976).

The endothelial cells grow very slowly as compared with other types of cells in the body. However, the proliferation of endothelial cells is induced by pro-angiogenic cytokines, activated hydrolytic enzymes which release the angiogenic mediators from extracellular matrix or the stimulation of angiogenic factors.

Generally, the process of angiogenesis is the degradation of basement membrane of blood vessels, the migration of endothelial cells, and the lumen formation via proliferation and differentiation of endothelial cells. One of the major events in the process of angiogenesis is a breakdown of the extracellular matrix before the formation of the capillary blood vessels. The most important enzyme of matrix degradation is matrix metalloproteinase (MMP).

When the failure in the regulation of angiogenesis occurs or MMPs are over activated, pathological angiogenesis takes place, which is related to many diseases (Polverini P J, Critical Reviews in Oral Biology, 6(3), 230-247(1995); Amp Das, et al., Progress in Retinal and Eye Research, 22 (2003) 721-748; Nick Di Girolamo, et al., IOVS, August 2001, Vol. 42, No. 9, 1963-1968; Patricia Lee, et al., Survey of ophthalmology, Vol 43, No. 3, November-December 1998, 245-269; D. B. Holland, et al., British Journal of Dermatology 2004, 150, 72-81; Anthony H Vagnucci Jr, et al., The Lancet, Vol 361, Feb. 15, 2003, 605-608; Berislav V. Zlokovic, Trends in Neuroscience, Vol. 28, No. 4, April 2005, 202-208; Jaap G. Neels, et al., The FASEB Journal express article 10. 1096403-1101fje. Published online Apr. 14, 2004; D. L. Crandall, et al., Microcirculation, 4, 1997, 211-232; G. Voros, et al., Endocrinology, 146, 2005, 4545-4554; M. A. Rupnick, et al., PNAS, 99, 2002, 10730-10735; E. Brakenhielm, et al., Circ. Res., 94, 2004, 1579-1588; H. R. Lijnen, et al., Arterioscler Thromb Vasc Biol., 22. 2002, 374-379; D. Demeulemeester, et al., Biochem. Biophys. Res. Commun., 329, 2005, 105-110, etc.) such as, Cancer growth and metastasis;

Angioma, angiofibroma, vascular deformity, and cardiovascular diseases such as atherosclerosis, angiostenosis, edemic sclerosis and stenosis;

Opthalmological diseases such as diabetic retinopathy, macular degeneration (including age-related macular degeneration), pterygium, retinal degeneration, angiogenesis in corneal implantation, angiogenic glaucoma, angiogenic corneal diseases such as corneal synechia and iris synechia, retrolental fibroplasias, granular conjunctivitis, corneal ulcer, proliferate vitreous body retinopathy, immature retinopathy, eye inflammation in eyes, conical cornea, Sjogren's syndrome, myopia, eyes tumors and rejection in cornea implantation;

Obesity;

Chronic inflammatory diseases such as arthritis, rheumatoid arthritis, osteoarthritis, septic arthritis, MMP-mediated osteopathy and degenerative cartilage loss following traumatic joint injury;

Inflammation diseases such as inflammation of the central nervous system and inflammatory bowel disease;

Dermatological disease such as psoriasis, telangiectasis, pyogenic granuloma, seborrheic dermatitis and acne;

Alzheimer's disease;

Corneal synechia, proteinuria, abdominal aortic aneurysm, demyelinated nerve tissue, liver fibrosis, nephroglomerular disease, premature rupture of the fetal membrane, periodontal diseases such as gingivitis and periodontitis.

In particular, angiogenesis plays very important role in growth and metastasis of cancer cells. New blood vessels supply not only nutrients and oxygen to fast-growing cancer cells, but also provide access to the circulation for the evolution of metastasis [Folkman and Tyler, Cancer Invasion and metastasis, Biologic mechanisms and Therapy (S. B. Day ed.) Raven press, New York, 94-103(1977); Polverini P J, Critical Reviews in Oral Biology, 6(3), 230-247 (1995)].

Cancer patients die because of metastasis, and chemotherapy and immunotherapy currently used in the treatment of cancer can not contribute to the survival of cancer patients due to the lack of anti-metastasis effects.

Arthritis, a well-known inflammatory disease, is initiated as an autoimmune disease. However, the growth of vascular endothelial cell in the synovial cavity is activated by the inflammatory cytokines, which finally destroyed cartilage in the articulation. In other words, the proliferation of synovial cells and endothelial cells in synovial cavity with the help of cytokines inducing inflammation induces angiogenesis and pannus formation, which are the major role in destroying cartilage (Kocb A E, Polverini P J and Lcibovich S J, *Arth Rheum* 29, 471-479, 1986; Stupack D G, Storgard C M and Cheresh D A, Braz *J Med Biol Rcs* 32, 578-581, 1999 Koch A E, *Arthritis Rheum* 41, 951-962, 1998). Meanwhile, it has also been shown that stromelysin in arthritis and traumatic joint injury is recognized to play an important role in the activation of procollagenase to active collagenase [Murphy, G. et al., Biochem. J. 248, 265~268(1987)]. Therefore, the downregulation of MMP activity can prevent the progress of arthritis.

Many people are losing their eyesight all over the world because of various ocular diseases. Many patients become blind due to the infiltration of the capillary blood cells into the vitreous humor (Jeffrey M I and Takayuki A, *J Clin Invest* 103, 1231-1236, 1999). Age-related macular degeneration, diabetic retinopathy, retinopathy of prematurity, angiogenic glaucoma, angiogenic corneal diseases are typical angiogenic ocular diseases [Adamis A P, Aiello L P and D'Amato R A, Angiogenesis 3, 9-14(1999)]. Diabetic retinopathy, a complication of diabetes, is caused by the rupture of capillaries and by the covering of hemorrhage on the surface of retina.

Collagenase, gelatinase and stromelysin have been implicated in the destruction of the extracellular matrix of the cornea. This is thought to be an important mechanism of morbidity and visual loss in a number of ulcerative ocular diseases, particularly those following infection or chemical damage (Burns, F. R. et al., *Invest Opthalmol and Visual Sci*, 32, 1569-1575, 1989). The MMPs present in the eye during ulceration are derived either endogenously from infiltrating leucocytes or fibroblasts, or exogenously from microbes.

Psoriasis is caused by extremely active proliferation of keratinocytes. Fast-growing cells require sufficient blood supply, and angiogenesis is abnormally induced in psoriasis (Folkman J., *J Invest Dermatol* 59, 40-48, 1972).

Collagenases, secreted by inflammatory stimulation and microbes, decompose the collagen in gingival connective tissue and finally cause periodontitis. Collagenase and stromelysin activities have been identified in fibroblasts isolated from inflamed gingiva and the levels of enzyme have been correlated with the severity of the gingivitis observed (Beeley, N. R. A. et al., supra Overall, C. M. et al., *J Periodontal Res*, 22, 81-88, 1987).

MMPs are correlated with the pathogenesis of CNS (Central Nerve System), which destroy myelin or blood-brain barrier. MMP is also reported to be related to the accumulation of amyloid beta protein in Alzheimer's disease [Yong, V W. et al., Trends Neurosci 21(2), 75-80(1998)].

Excessive levels of gelatinase-B in cerebrospinal fluid has been linked with incidence of multiple sclerosis and other neurological disorders [Beeley, N. R. A. et al., supra.; Miyazaki, K. et al., Nature 362, 839~841(1993)], and contribute to degradation and the accumulation of amyloid beta protein [Backstrom J R, et al., J neurosci 16(24), 7910-9 (1996)].

Recent reports have also shown that MMP-1 activity is highly induced in the brain of Alzheimer's disease, and MMP-3 which activates the proenzyme of MMP is also involved in the pathophysiology of the disease (Leake A, Morris C M, & Whateley, *J Neurosci Lett* 291, 201-3, 2000; Yoshiyama Y, Asahina M, & Hattori T, *Acta Neuropathol (berl)*, 99, 91-5, 2000).

The degradation of basement membrane by MMP is very important procedure for cancer invasion, metastasis and also angiogenesis. So, the overexpression of MMP can stimulate angiogenesis, cancer invasion and metastasis.

In the case of adenocarcinoma, invasive proximal gastric cancer cells express the 72-kD form of type IV collagenase [Schwartz, G. K. et al., Cancer 73, 22~27(1994)]. Rat embryo cells transformed by the Ha-ras and v-myc oncogenes or by Ha-ras alone are metastatic in nude mice and release the 92 kDa gelatinase/collagenase (MMP-9) [Bernhard, E. J. et al., Proc. Natl. Acad. Sci 91, 4293~4597 (1994)].

Therefore, angiogensis inhibitors or MMP inhibitors can be developed for the therapeutics of these diseases.

In relation to this, the inventors disclosed at KR registration No. 10-550,298 that *Melissa* leaf extract had antiangiogenic effect through in vitro assay such as HUVEC (Human Umbilical Vein Endothelial cell) tube formation, and in vivo assay such as mouse Matrigel model and CAM assay.

Furthermore, the inventors disclosed at KR registration No. 10-473,688 that *Melissa* leaf extract had inhibition effect on MMP (matrix metalloproteinase) which is important to degrade the basement membrane in the process of angiogenesis.

The inventors bring to completion this invention through research to obtain more active *Melissa* leaf fraction having excellent angiogenesis and MMP inhibitory activities.

SUMMARY OF THE INVENTION

It is an objection of the present invention to provide an ethyl acetate fraction of *Melissa* leaf having excellent angiogenesis and MMP inhibitory activities, and a composition comprising the same.

In one aspect, the present application is directed to an ethyl acetate fraction of *Melissa* leaf, having angiogenesis and MMP inhibitory activities. The *Melissa* leaf may be extracted with 50~100% $C_1$~$C_6$ alcohol, and concentrated, and then the concentrated alcohol extract may be suspended in water, and fractionated with ethyl acetate, and dried to obtain the ethyl acetate fraction of *Melissa* leaf. The $C_1$~$C_6$ alcohol may be 70-80% $C_1$~$C_6$ alcohol. The $C_1$~$C_6$ alcohol may be ethanol or methanol.

In another aspect, the invention is directed to a composition for the prevention or treatment of obesity, including the ethyl acetate fraction of *Melissa* leaf described above. The composition may be used for the prevention or treatment of diabetic retinopathy, macular degeneration (including age-related macular degeneration), pterygium, retinal degeneration, corneal graft neovascularization, neovascular glaucoma, neovascular corneal disease, retrolental fibroplasia, trachoma, corneal ulcer, proliferative vitreoretinopathy, immature retinopathy, ocular inflammation, keratoconus, sjogren's syndrome, myopia, ocular tumor or graft rejection after keratoplasty. Prevention or treatment of cancer growth and metastasis, may also occur, as with prevention or treatment of haemangioma, angiofibroma, vascular malformation, arteriosclerosis, vascular adhesion, scleroderma, or restenosis. Prevention or treatment of arthritis, rheumatoid arthritis, osteoarthritis, septic arthritis, MMP-mediated osteopenia, or degenerative cartilage loss following traumatic joint injury may also be carried out by the use of the ethyl acetate extract of *Melissa* described above.

In another aspect, the invention is directed to a composition for the prevention or treatment of inflammatory diseases of the central nervous system or inflammatory bowel disease using the ethyl acetate fraction of *Melissa* leaf described above. Prevention or treatment of psoriasis, telangiectasia, pyogenic granuloma, seborrheic dermatitis, or acne, using the ethyl acetate fraction of *Melissa* leaf described above is encompassed in the present invention. Prevention or treatment of Alzheimer's disease is also included. Prevention or treatment of abnormal wound concrescence, proteinuria, abdominal aortic aneurysm, demyelinated nerve tissue, liver fibrosis, nephroglomerular diseases, premature rupture of the fetal membrane, or periodontal diseases is also included. The inventive composition may be formulated in a dosage form of granule, powder, tablet, coated tablet, capsule, pill, syrup, drop, liquid, solution, suspension, emulsion, or injectable solutions.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1A:
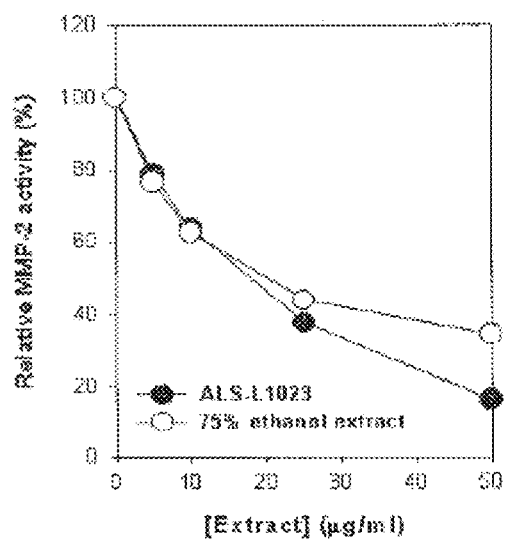
FIG. 1A and FIG. 1B are graphs showing the inhibitory effect of ALS-L1023 on MMP activity.

In the present application, "a" and "an" are used to refer to both single and a plurality of objects.

The present invention provides an ethyl acetate fraction of *Melissa* leaf having excellent angiogenesis and matrix metalloproteinases (MMPs) inhibitory activities. In one specific embodiment of the invention, an alcohol extract, preferably 75% ethanol, of *Melissa* yielded advantageous anti-angiogenesis effects compared with the water extract of *Melissa*. Moreover, further fractionating the alcohol extract of *Melissa* with ethyl acetate resulted in an extract having even greater anti-angiogenesis and MMP inhibiting effects compared with *Melissa* preparations of alcohol extraction alone. Preferably, the extract of *Melissa* obtained by first alcohol extraction and then ethyl acetate fractionation may be used to prevent or treat disorders or diseases caused by angiogenesis. Thus, in one aspect, the present invention is also directed to providing a composition comprising the ethyl acetate fraction of *Melissa* leaf for the treatment or prevention of angiogenesis-related diseases and MMP-mediated diseases.

Hereinafter, the present invention is described in detail.

The ethyl acetate fraction of *Melissa* leaf according to the present invention is characterized in that *Melissa* leaf is extracted with 50~100% $C_1$~$C_6$ alcohol, and concentrated, and then the concentrated alcohol extract is suspended in water, and fractionated with ethyl acetate, and dried to obtain the ethyl acetate fraction of *Melissa* leaf.

In the method of producing an ethyl acetate fraction of *Melissa* leaf according to the present invention, dried or non-dried or the mixture of *Melissa* leaf can be used. For the effective extraction, *Melissa* leaf can be cut into small pieces or pulverized.

An alcohol extract of *Melissa* leaf can be extracted by conventional methods. The used extraction solvent may be 50~100% alcohol, preferably 70~80% alcohol of 5~10 volume to *Melissa* leaf. The alcohol may be $C_1$~$C_6$ alcohol, preferably methanol, ethanol or a mixture thereof.

In the examples of the present invention, 75% ethanol extract of *Melissa* leaf is suspended in water, and fractionated with ethyl acetate, and dried to obtain the ethyl acetate fraction of *Melissa* leaf (called ALS-L1023).

Water-soluble materials and water-insoluble materials can be extracted effectively by the use of 50~100% alcohol as extraction solvent. And this method is effective to obtain water-insoluble material which is soluble in ethyl acetate.

Ethyl acetate is selected as a second extraction solvent considering product yield, toxicity of residues and the relative content of reference substances.

For the mass production of the fraction from *Melissa* leaf with excellent anti-angiogenic activity, 50~100% alcohol extract of *Melissa* leaf is suspended in water, and fractionated with ethyl acetate, and dried to obtain the ethyl acetate fraction of *Melissa* leaf (called ALS-L1023 in the following examples).

Also, *Melissa* leaf may be extracted with 50~100% $C_1$~$C_6$ alcohol, dried, and the alcohol extract suspended in water, and then fractionated with ethyl acetate, dried, and the ethyl acetate fraction resuspended in water, and dried to obtain the ethyl acetate fraction of *Melissa* leaf.

The ethyl acetate fraction of *Melissa* leaf obtained was used in animal test and preclinical test.

The inventors discovered that an ethyl acetate fraction of *Melissa* leaf according to this invention is excellent in inhibiting angiogenesis and MMP activities comparing with other fractions obtained by other solvent partition. The ethyl acetate fraction of *Melissa* leaf shows the most effective and excellent activities in angiogenesis inhibition through MMP inhibition assay, HUVEC tube formation assay, and mouse Matrigel implant assay. The inventors also found that this fraction inhibited obesity by reducing adipose tissue, adipose cell size and inducing gene expression related to fatty acid oxidation.

It is therefore clear that an ethyl acetate fraction of *Melissa* leaf according to the present invention can be used as an anti-angiogenic agent and MMP-inhibitory agent for the treatment or prevention of angiogenesis-related diseases and MMP-mediated diseases.

Therefore the present invention provides a composition comprising an ethyl acetate fraction of *Melissa* leaf.

The angiogenesis-related diseases and MMP-mediated diseases that can be treated or prevented by the composition of the present invention include, but are not limited to, cancer growth and metastasis; angioma, angiofibroma, vascular deformity, and cardiovascular diseases such as atherosclerosis, angiostenosis, edemic sclerosis and stenosis; opthalmological diseases such as diabetic retinopathy, macular degeneration (including age-related macular degeneration), pterygium, retinal degeneration, angiogenesis in corneal implantation, angiogenic glaucoma, angiogenic corneal disease such as corneal synechia and iris synechia, retrolental fibroplasias, granular conjunctivitis, corneal ulcer, proliferate vitreous body retinopathy, immature retinopathy, eye inflammation in eyes, conical cornea, Sjogren's syndrome, myopia, eyes tumors and rejection of cornea implantation; obesity; chronic inflammatory diseases such as arthritis, rheumatoid arthritis, osteoarthritis, septic arthritis, inflammation diseases such as inflammation of the central nervous system and inflammatory bowel disease; MMP-mediated osteopathy and regressive cartilage loss; dermatological disease such as psoriasis, telangiectasis, pyogenic granuloma, seborrheic dermatitis and acne; Alzheimer's disease; corneal synechia, proteinuria, abdominal aortic aneurysm, demyelinated nerve tissue, liver fibrosis, nephroglomerular disease, premature rupture of the fetal membrane, periodontal diseases such as gingivitis and periodontitis.

The composition of the present invention can be used in combination with known anti-angiogenic agents or known MMP inhibitors.

In the present invention, the composition comprising the ethyl acetate fraction of *Melissa* leaf which is used as an agent for the treatment or prevention of angiogenesis-related diseases and MMP-mediated diseases, can be pharmaceutical composition or food composition.

The pharmaceutical composition of the present invention can also comprise pharmaceutically and physiologically acceptable additives such as diluent, dispersing agent, surfactant, solvent, disintegrating agent, sweetener, binder, coating agent, blowing agents, lubricants, glidants or flavoring agent.

The pharmaceutical composition comprising the ethyl acetate fraction of *Melissa* leaf of the present invention as an active ingredient can be formulated in combination with pharmaceutically acceptable excipients, carriers or diluents.

The pharmaceutical composition of the present invention can be formulated in any form such as granule, powder, tablet, coated tablet, capsule, pill, syrup, drop, liquid, solution, suspension, emulsion, or injectable solutions.

For example, in the composition of tablet or capsule type, the active ingredients can be bind with pharmaceutically acceptable inactive and non-toxic carriers. And adequate binders, lubricants, disintegrants and color formers can be included in case of need. Examples of suitable binders include, but are not limited to, starch, gelatin, dextrin, maltodextrin, natural sugar such as glucose or ß-lactose, corn sweetener, acacia, natural and synthetic gum such as tragacanth and sodium oleate, sodium stearate, magnesium stearate, sodium benzoate, sodium acetate, sodium chloride. Disintegrants include, but are not limited to, starch, methylcellulose, agar, bentonite, xanthan gum etc.

In the composition of liquid solution type, pharmaceutically acceptable carriers are saline, sterile water, Ringer's solution, buffered saline, albumin injection solution, dextrose solution, maltodextrin solution, glycerol, ethanol or mixed solution. And general additives like antioxidants, buffered solution, bacteriostat, etc. can be added to this composition. By using conventional method or the written text of Remington's pharmaceutical Science (Mack Publishing co, Easton Pa.), the composition of the present composition can be formulated in any desirable forms according to disease or ingredient.

Also, the food composition comprising the ethyl acetate fraction of *Melissa* leaf of the present invention as an active ingredient can be used as functional foods, dietary supplements or food additives. In case of food additives, the food composition of the present invention can be added to meat, drinking water, chocolate, groceries, snack, pizza, instant noodle, noodles, chewing gum, ice-cream, alcoholic beverage, vitamin complex, or healthy food.

The present invention provides the use of a composition comprising an ethyl acetate fraction of *Melissa* leaf for the treatment or prevention of angiogenesis-related diseases and MMP-mediated diseases. The composition of the present invention can be use in food and medicine for the treatment or prevention of angiogenesis-related diseases and MMP-mediated diseases.

The present invention also provides method for the treatment or prevention of angiogenesis-related diseases and MMP-mediated diseases comprising administering therapeutically effective amount of the ethyl acetate fraction of *Melissa* leaf to a mammal.

As used herein, "mammal" for purposes of treatment refers to any animal classified as a mammal, preferably, the mammal is human.

As used herein, "therapeutically effective amount" means an amount that will induce a biological or medical response in the animal or human, to which it is administered. An ordinarily skilled medical provider can determine the therapeutically effective amount, as well as, the appropriate dose and frequency of administration(s) to achieve an optimum clinical result. A therapeutically effective amount will vary depending on various factors such as kinds of diseases, severity of the patient's symptoms, contents of ingredients, age, body weight, sex of the individual patient, food, administration time, administration route, the ratio of the composition, treatment period, and other coadministered drugs. The composition of the present invention can be administered in a single dose, or as part of an administration regime such as multiple doses, desirable dosage of ethyl acetate fraction of *Melissa* leaf can be 3 mg/kg~250 mg/kg per day.

The composition of the present invention can be administered by various routes, for example, but without limitation, orally, rectally, intravenously, intraarterially, intraperitoneally, intramuscularly, intrarmucosally, subcutaneously, intradermally, transdermally, transcutaneously, intravaginally, intrarectally, nasally, ocularly, and/or intestinally.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—Production of Ethyl Acetate Fraction of *Melissa* Leaf

To produce *Melissa* leaf extract with potent anti-angiogenic activity, the *Melissa* leaf is extracted with distilled water, 50% aqueous ethanol, 75% aqueous ethanol, 100% ethanol and methanol, respectively. The crude extract was centrifuged, filtered, concentrated and then lyophilized to obtain an extract powder. The powder is stored at 4° C. until use. The anti-angiogenic effect of the extracts was tested by HUVEC tube formation assay at the concentration of 50 μg/Mℓ. As shown in Table 1, all the extract including water, 50%, 75%, 100% ethanol, and 100% methanol extracts showed inhibition effect in HUVEC tube formation assay. Especially, the 75% ethanol extract had relatively good inhibitiory activity comparing with other extracts, therefore 75% ethanol is selected as a primary extraction solvent.

TABLE 1

The effect of *Melissa* extracts on HUVEC tube formation

| Samples | HUVEC tube formation inhibition |
| --- | --- |
| Negative control | − |
| Water extract | + |
| 50% Ethanol extract | (+) |
| 75% Ethanol extract | +(+) |
| 100% Ethanol extract | + |
| 100% Methanol extract | +(+) |

−: tubes formed(no inhibition),
+/−: tubes almost resemble control(rare inhibition),
+: tubes are slightly disconnected(light inhibition),
++: tubes are heavily disconnected(significant inhibition),
+++: no tubes formed.

To find the most potent anti-angiogenic activity from *Melissa* leaf fractions, the 75% ethanol extract of *Melissa* leaf is sequentially partitioned with hexane, ethyl acetate, and butanol. Each fraction is centrifuged, filtered, concentrated and then lyophilized to obtain a fraction powder. The powder is stored at 4° C. until use. The anti-angiogenic effect was tested by HUVEC tube formation assay at the concentration of 50 μg/mℓ, respectively. As shown in Table 2, the ethyl acetate fraction has the most potent in anti-angiogenic activity.

TABLE 2

The effect of fractions on HUVEC tube formation

| Samples | HUVEC tube formation inhibition |
| --- | --- |
| Negative control | − |
| 75% Ethanol extract | +(+) |
| Hexane fraction | +/− |
| Ethyl acetate fraction | ++(+) |
| Butanol fraction | + |

−: tubes formed(no inhibition),
+/−: tubes almost resemble control(rare inhibition),
+: tubes are slightly disconnected(light inhibition),
++: tubes are heavily disconnected(significant inhibition),
+++: no tubes formed.

Based on the results of these assay, mass production of *Melissa* leaf fraction with excellent anti-angiogenic activity was performed as follows; 75% ethanol extract of *Melissa* leaf is suspended in water, and fractionated with ethyl acetate, and dried to obtain the ethyl acetate fraction of *Melissa* leaf (called ALS-L1023 in the following examples). This ALS-L1023 was used for animal test and preclinical test.

Detailed mass production procedure of ALS-L1023 is described below.

The dried 100 kg of *Melissa* leaf was extracted twice with 350 L of 75% aqueous ethanol at 83° C. for 4 hours. The extract was filtered with 10 μm filter and concentrated to 30 L and then fractionated with 40 L ethyl acetate two times. After washing this fraction with distilled water, it was concentrated to the volume 15 L and then dried with hot wind at 45° C. Finally, the 5 kg of ALS-L1023 was obtained in a dried powder form.

Example 2—Production of Ethyl Acetate Fraction of *Melissa* Leaf (1) MMP Inhibition Assay In order to investigate MMP inhibition by ALS-L1023 produced by mass production, MMP enzyme activity assay was performed by a spectrofluorometric method (Perkin-Elmer LS50B).

Human MMP enzymes used in the assay were prepared by recombinant protein production using baculovirus system in AngioLab, Inc. Fluorometric substrate (Bachem Cat. No. M-2105) was used as the substrate for MMP-2 and MMP-9. ALS-L1023 was added with various concentrations to the reaction buffer containing MMP enzyme and substrate, and fluorescence intensity was measured. The $IC_{50}$ of ALS-L1023 for MMP-2 and MMP-9 was 17.7±1.0 μg/Mℓ and 12.3±1.4 μg/Mℓ respectively.

Figure 1B:
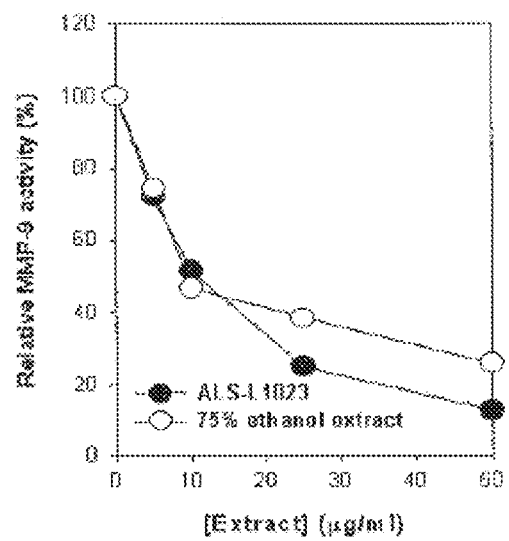

The $IC_{50}$ of 75% ethanol extract of *Melissa* leaf for MMP-2 and MMP-9 was 33.6±1.5 μg/Mℓ and 26.0±1.7 μg/Mℓ respectively. Thus it is confirmed that the MMP inhibition activity of ALS-L1023 was enhanced comparing with that of 75% ethanol extract of *Melissa* leaf (FIG. 1).

(2) HUVEC Tube Formation Inhibitory Activity

The HUVEC (Human Umbilical Vein Endothelial Cell) tube formation assay is an in vitro assay that is closely related to in vivo efficacy, and the effect of ALS-L1023 on HUVEC tube formation was investigated.

Figure 2:
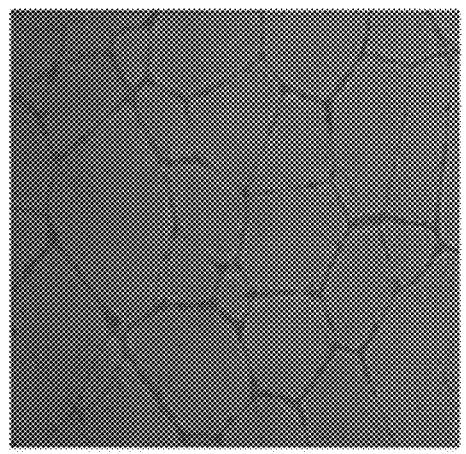
FIG. 2 is a photograph showing the inhibitory effect of ALS-L1023 on HUVEC tube formation.
Figure 2:
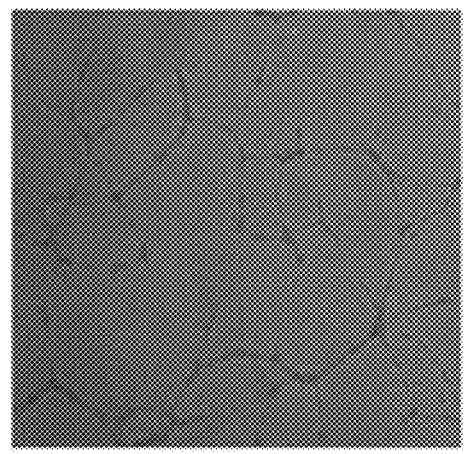

To perform the tube formation assay, HUVECs were isolated from freshly obtained umbilical cords. Cells were cultured and identified by immunocytochemical staining with anti-Factor VIII antibody. HUVECs cultured within passage 5 were grown on Matrigel (BD Bioscience, Bedford, Mass., USA) at 37° C. in the absence or presence of different concentrations of ALS-L1023 for 18 hours. Tube formation was observed using microscope. As shown in FIG. 2, ALS-L1023 produced by mass production inhibited tube formation at 50 μg/Mℓ. Capillary network of tubes was disconnected by ALS-L1023 while capillary network of tubes was observed in control. Moreover, ALS-L1023 inhibited HUVEC tube formation in a dose dependent manner as shown in Table 3.

TABLE 3

Inhibition of HUVEC tube formation by ALS-L1023

| sample(μg/Ml) | HUVEC tube formation inhibition |
| --- | --- |
| 0(control) | − |
| 25 | + |

TABLE 3-continued

Inhibition of HUVEC tube formation by ALS-L1023

| sample(μg/Ml) | HUVEC tube formation inhibition |
|---|---|
| 50 | ++ |
| 100 | ++ |

(3) Cell Cytotoxicity Test

To test the cytotoxicity of ALS-L1023 on HUVEC, 5,000-10,000 as seeded in 96 well plate and ALS-L1023 of different concentrations was added to each well. The cell viability was tested with XTT tetrazolium base (sodium 3'-[1-(phenylaminocarbonyl)-3,4-tetrazoium]-bis[4-methoxy-6-nitro]benzene sulfonic acid hydrate) cell proliferation kit (Roche, Germany) and viable cells were measured by ELISA plate reader. ALS-L1023 did not affect HUVEC viability at the concentration of 50 μg/Mℓ showing HUVEC tube formation inhibition.

(4) Mouse Matrigel Assay

Mouse Matrigel implant assay was performed to measure the inhibition of in vivo angiogenesis by ALS-L1023 quantitatively.

A 0.4 ml of Matrigel containing 50 ng/ml of basic fibroblast growth factor (bFGF) and 50 units/ml of heparin was implanted by subcutaneous injection into C57BL/6 mouse. 0.5 mg of ALS-L1023 dissolved in 10% ethanol per mouse was orally administered twice a day for 4 days. 10% ethanol was orally administered to control group. At day 5, an epidermis of mouse was removed, and Matrigel was recovered, and then the amount of hemoglobin in the Matrigel was determined by Drabkin's reagent (Sigma, USA).

Figure 3:
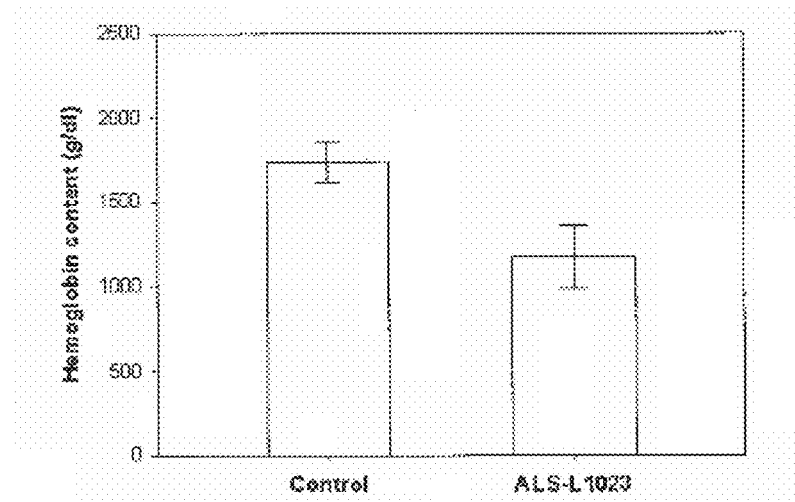
FIG. 3 is a graph that shows the result of mouse Matrigel assay for analyzing the inhibitory effect of ALS-L1023 on angiogenesis.

As shown in FIG. 3, the hemoglobin contents in Matrigel recovered from ALS-L1023 treated group were decreased as compared with the vehicle control group. The percent of angiogenesis inhibition by ALS-L1023 was 33%.

FORMULATION EXAMPLES

Suitable excipients were added to ALS-L1023 to improve its stability, and then 250 mg thereof was packed in a hard capsule. The mixing ratio is described in the following Table 4.

TABLE 4

Formulation ratio of ALS-L1023

| Raw material | mixing ratio (%) |
|---|---|
| ALS-L1023 | 60 |
| Magnesium stearate | 1 |
| Colloidal silicon dioxide | 1 |
| Microcrystalline cellulose | 33 |
| Sodium lauryl sulfate | 5 |

Example 3—Anti-Obesity Effect of ALS-L1023 Fraction

With respect to high fat diet-induced obesity, the following experiment was performed to examine the inhibitory effect of ALS-L1023 on abdominal fat. The formulated ALS-L1023 as an active ingredient was mixed with a 45 kcal % high fat feed (manufactured by Research Diets Inc., USA) in a content of 0 (control group), 0.1% (low), 0.25% (medium), and 0.5% (high) (formulated form: 0, 0.17, 0.42, 0.83%). For the preparation of the control group containing no active ingredient ALS-L1023, excipients contained in the formulated ALS-L1023 were mixed with the high fat feed in a content of 0.33% as a high dose. After a one-week acclimation period, 7-week-old male SD rats were divided into groups of 7 mice per group, and fed for 12 weeks. Then, their body weight and weight of abdominal fat were measured, and biochemical blood tests and histopathological tests of liver and adipose tissue were performed.

(1) Body Weight

Body weight was measured on the day of acquisition, initiation day of administration, once every week after initiation of the administration, and the day of autopsy. The results are summarized in Table 5, in which the mean body weight of the vehicle control group constantly increased from 204.73±5.57 g (before administration) to 633.63±43.08 g (for 12 weeks after administration), and the mean body weight of ALS-L1023 group (low, medium, and high dose groups) constantly increased from 210.10±5.19 g, 204.97±6.61 g, and 208.01±7.65 g (before administration) to 623.72±58.02 g, 588.69±33.76 g, and 584.83±33.44 g (for 12 weeks after administration). There was no statistical significance between the vehicle control and ALS-L1023 groups. However, the mean body weight of ALS-L1023 group decreased in a dose-dependent manner.

TABLE 5

Changes in body weight by administration of ALS-L1023

| ALS-L1023 content (%) | 0 (control group) | 0.1 (low dose group) | 0.25 (medium dose group) | 0.5 (high dose group) |
|---|---|---|---|---|
| Body weight before administration (g) | 204.73 ± 5.57 | 210.10 ± 5.19 | 204.97 ± 6.61 | 208.01 ± 7.65 |
| Body weight after administration (g) | 633.63 ± 43.08 | 623.72 ± 58.02 | 588.69 ± 33.76 | 584.83 ± 33.44 |

(2) Feed Intake

Daily feed intake was determined as follow. The feeder was filled with powdery feed, and then its weight was measured. At 24 hrs after feeding the animals with the feeder, the weights were measured, and a difference in the measured weights was determined as a daily feed intake. The measurement was performed on the initiation day of the administration, and once every week after initiation of the administration.

Mean daily feed intake of the vehicle control group was within a range of 18.46 to 22.73 g for 12 weeks, and mean daily feed intakes of low, medium, and high dose groups were within a range of 17.14 to 21.84 g, 17.29 to 22.03 g and 16.99 to 20.84 g, respectively. There was no significant difference, as compared with the vehicle control group.

(3) Organ and Adipose Tissue Weights

Before autopsy and blood collection, the animals were fasted for a period of 18 hrs or more, and anesthetized with ether, followed by blood collection and phlebotomy. The mesenteric adipose tissues, epididymal adipose tissues, and retroperitoneal adipose tissues were excised from the abdominal cavity, and weighed. The liver, heart, kidney, spleen, and pancreas were weighed.

As a result, there was no significant difference in the weights of heart, liver, pancreas, kidney (left, right) and spleen between the vehicle control and experimental groups. With respect to the mesenteric adipose tissue weight, the low, medium and high dose groups were 15.90±4.36 g, 12.64±1.69 g, and 11.23±3.32 g, respectively. That is, the experimental groups were decreased in a dose-dependent manner, compared with the vehicle control group of 15.16±4.41 g. With respect to epididymal adipose tissue weight, the low, medium and high dose groups were 17.74±3.37 g, 16.29±2.62 g, and 15.67±3.83 g, respectively. That is, the experimental groups were decreased in a dose-dependent manner, compared with the vehicle control group of 20.80±4.41 g, and a statistically significant difference ($p<0.05$) was observed in the high dose group. With respect to retroperitoneal adipose tissue weight, the low, medium and high dose groups were 27.20±5.76 g, 21.36±4.03 g, and 23.94±6.24 g, respectively. That is, the experimental groups were decreased in a dose-dependent manner, compared with the vehicle control group of 29.73±3.23 g, and a statistically significant difference ($p<0.05$) was observed in the medium dose group. With respect to a total weight of the abdominal adipose tissue including the mesenteric adipose tissue, the epididymal adipose tissue and the retroperitoneal adipose tissue, the low, medium and high dose groups were 60.84±11.66 g, 50.29±7.31 g, and 50.84±11.84 g, respectively. That is, the experimental groups were decreased, compared with the vehicle control group of 65.69±10.13 g, and a statistically significant difference ($p<0.05$) was observed in the medium and high dose groups (see Table 6).

TABLE 6

Changes in organ and adipose tissue weights by administration of ALS-L1023

| ALS-L1023 content (%) | 0 (control group) | 0.1 (low dose group) | 0.25 (medium dose group) | 0.5 (high dose group) |
| --- | --- | --- | --- | --- |
| mesenteric adipose tissue weight (g) | 15.16 ± 4.41 | 15.90 ± 4.36 | 12.64 ± 1.69 | 11.23 ± 3.32 |
| epididymal adipose tissue weight (g) | 20.80 ± 4.41 | 17.74 ± 3.37 | 16.29 ± 2.62 | 15.67 ± 3.83** |
| retroperitoneal adipose tissue weight (g) | 29.73 ± 3.23 | 27.20 ± 5.76 | 21.36 ± 4.03** | 23.94 ± 6.24 |
| total weight of abdominal adipose tissue (g) | 65.69 ± 10.13 | 60.84 ± 11.66 | 50.29 ± 7.31** | 50.84 ± 11.84** |

**$p < 0.05$ compared with the control group (4) Biochemical Blood Tests

In the biochemical blood tests, there was no significant difference in liver indices, such as serum levels of AST (Aspartate aminotransferase), ALT (Alanine aminotransferase), and ALP (Alkaline phosphatase) between the control and experimental groups. With respect to total blood cholesterol level, the low, medium and high dose groups were 88.07±14.35 mg/dL, 86.96±17.68 mg/dL, and 79.90±10.45 mg/dL, respectively. That is, the experimental groups were decreased in a dose-dependent manner, compared with the vehicle control group of 102.09±21.82 mg/dL. With respect to triglyceride level, the low, medium and high dose groups were 50.93±15.28 mg/dL, 46.63±11.77 mg/dL, and 45.50±22.45 mg/dL, respectively. That is, the experimental groups were also decreased in a dose-dependent manner, compared with the vehicle control group of 58.13±25.04 mg/dL. With respect to LDL level, the low, medium and high dose groups were 9.56±2.67 mg/dL, 9.11±2.92 mg/dL, and 8.56±2.26 mg/dL, respectively. That is, the experimental groups were also decreased in a dose-dependent manner, compared with the vehicle control group of 12.31±3.70 mg/dL. However, there was no significant difference in the levels of glucose, total protein, and albumin between the control and experimental groups. Thus, with regard to ALS-L1023 administration, the serum levels in total cholesterol, triglyceride, and LDL of the experimental groups were decreased in a dose-dependent manner, compared with the vehicle control group (see Table 7).

TABLE 7

Changes in blood biochemical indices by administration of ALS-L1023

| ALS-L1023 content (%) | 0 (control group) | 0.1 (low dose group) | 0.25 (medium dose group) | 0.5 (high dose group) |
| --- | --- | --- | --- | --- |
| total cholesterol (mg/dL) | 102.09 ± 21.82 | 88.07 ± 14.35 | 86.96 ± 17.68 | 79.90 ± 10.45 |
| triglyceride (mg/dL) | 58.13 ± 25.04 | 50.93 ± 15.28 | 46.63 ± 11.77 | 45.50 ± 22.45 |
| LDL (mg/dL) | 12.31 ± 3.70 | 9.56 ± 2.67 | 9.11 ± 2.92 | 8.56 ± 2.26 |

(5) Histopathological Test of Liver

The livers were weighed, and then fixed in 10% neutral buffered formalin solution, followed by routine histological processing. Tissue slide samples were prepared, and then stained with H&E, followed by observation under a microscope for hepatic steatosis. As a result, in the vehicle control group, excessive accumulation of fat globules was observed in hepatic lobule of hepatocyte, which is the finding of hepatic steatosis. The microvesicular or macrovesicular fatty changes were mainly observed around the hepatic portal vein. Inflammatory cell infiltration that occurs at an advanced stage of hepatic steatosis mainly occurred between or around ballooned hepatocytes where hepatic steatosis occurred. At a moderate grade of hepatic steatosis, inflammatory cell infiltration occurred around central veins. Other abnormal pathological findings were not observed.

In the low dose group, hepatic steatosis was also observed, which was similar to that observed in the vehicle control group. In the medium dose group, the slightly decreased hepatic steatosis and inflammatory cell infiltration were observed, as compared with the vehicle control and low dose groups.

Figure 4:
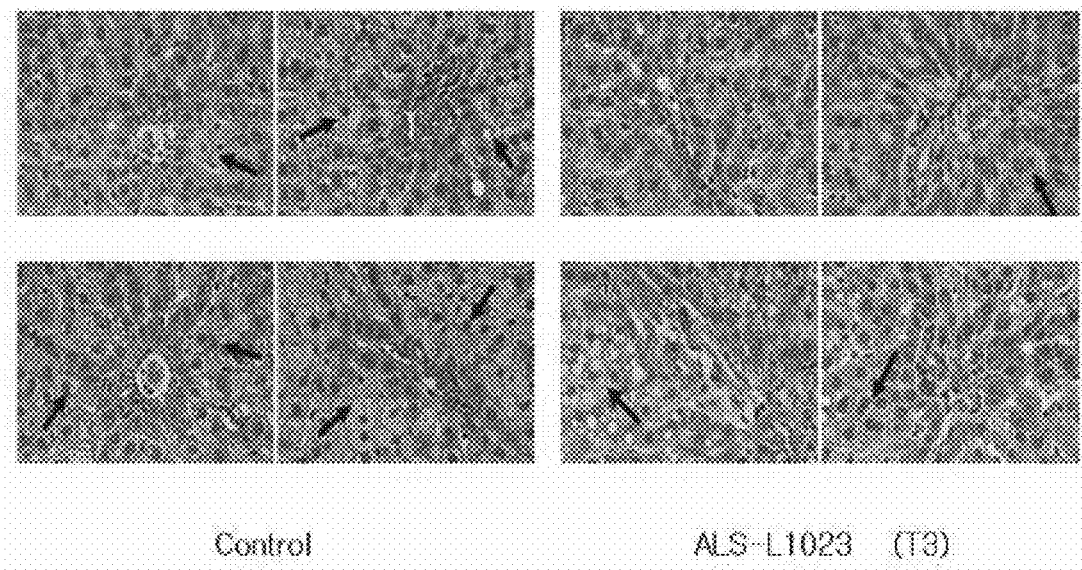
FIG. 4 is microscopical photographs of liver tissue showing the reduction in hepatic steatosis and inflammatory cell infiltration upon feeding high fat diet-induced obese rats with a high dose of ALS-L1023 compared with the vehicle control group.

In the high dose group, the inhibition of hepatic steatosis or decreased inflammatory cell infiltration was observed, which was similar to that observed in the medium dose group (see FIG. 4). This result suggests that ALS-L1023 exerted the inhibitory effects thereon.

(6) Adipocyte Area in Adipose Tissue

Figure 5:
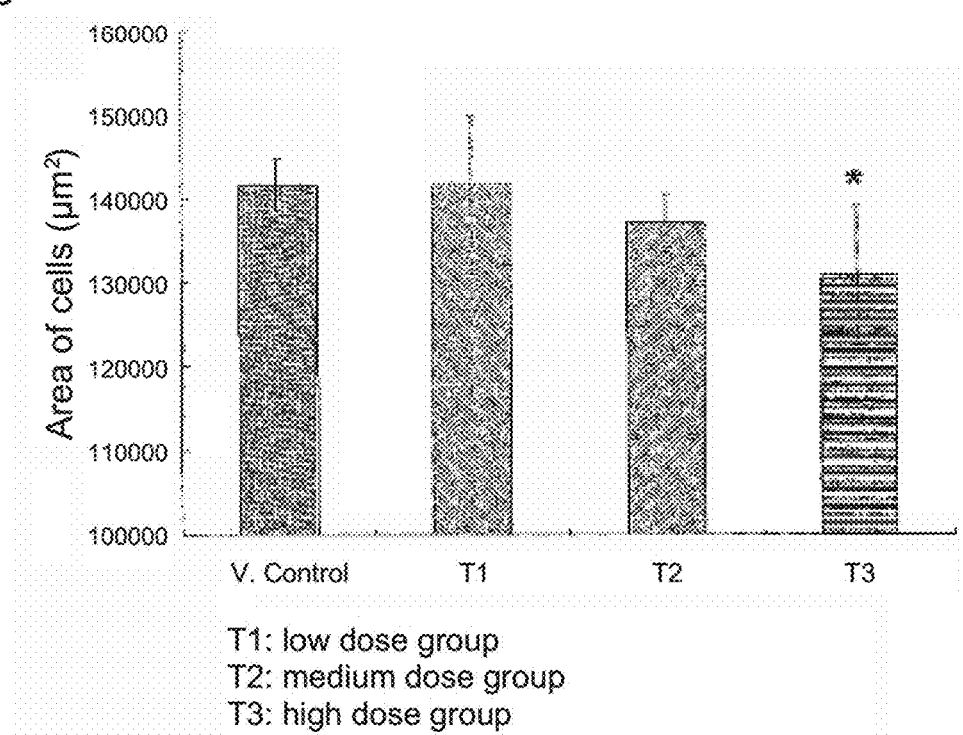
FIG. 5 is a graph showing the reduction of adipocyte area in retroperitoneal adipose tissue upon feeding high fat diet-induced obese rats with a medium and high dose of ALS-L1023 compared with the vehicle control group.

The excised retroperitoneal adipose tissues were weighed, and then paraffin-embedded tissue samples were prepared by routine histologic processing, followed by H&E staining. 5 sampling sites were randomly chosen, and mean value of 10 adipocyte areas adjacent to each sampling site were determined as an adipocyte area of each subject using stereo investigator software (MicroBrigthField, VT, USA) connected to an optical microscope. As shown in FIG. 5, the reduction in the adipocyte area was observed in the medium and high dose groups, as compared with the vehicle control group. A statistically significant difference (p<0.05) was observed in the high dose group.

Taken together, when high fat diet-induced obese rats were fed with ALS-L1023 for 12 weeks, ALS-L1023 exerted inhibitory effects of obesity, including the reduction in the abdominal adipose tissue weight and in the serum levels of total cholesterol and triglyceride, the alleviation of hepatic steatosis, and the reduction in adipocyte size.

Example 4—Effect of ALS-L1023 on Neovascular Ocular Diseases

In order to evaluate the efficacy of ALS-L1023 on retinal neovascularization, Oxygen-induced retinopathy mice in ROP (retinopathy of prematurity) animal model were intraperitoneally injected with diluted ALS-L1023 in DMSO at a dose of 25 mg/kg on day 13 after birth for a period of 5 days.

As a result, retinal neovascularization and many abnormal blood vessels were observed in the ROP control group, whereas normal retinas show uniform and compact patterns of blood vessels. Notably, reduced neovascularization in the central retina and peripheral retina and the lower number of abnormal blood vessels were observed in the ALS-L1023 group, as compared with the ROP control group. Thus, ALS-L1023 is expected to be effective in preventing and treating the ocular neovascularization.

Example 5—Effect of ALS-L1023 on Macular Degeneration

Figure 6:
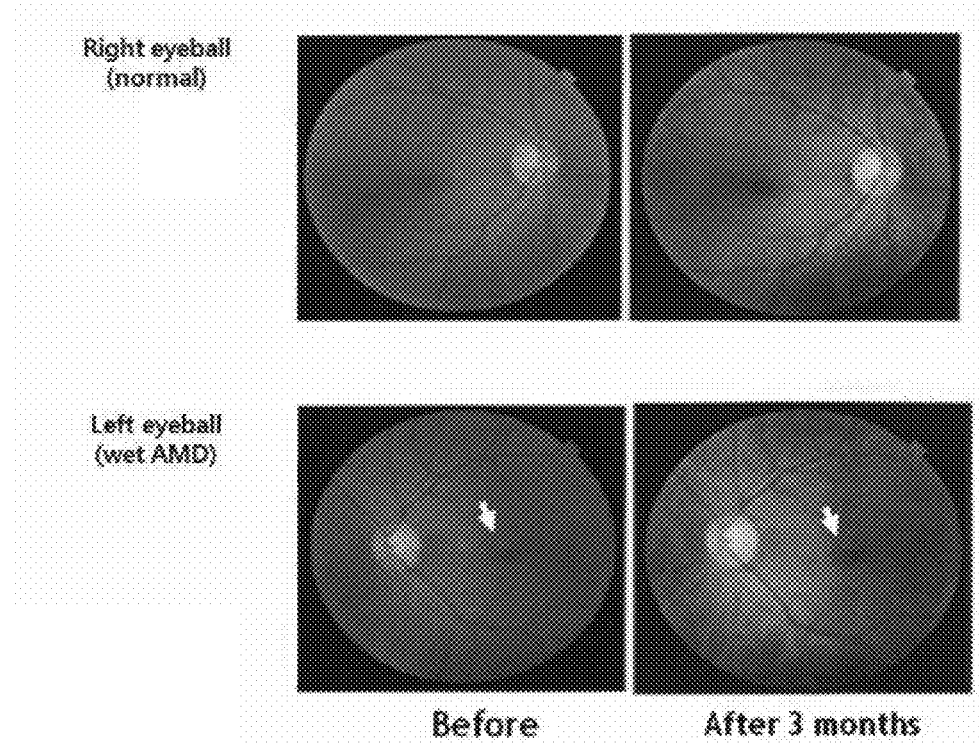
FIG. 6 is a photograph showing the inhibitory effect of ALS-L1023 on progression of exudative age-related macular degeneration by oral administration of ALS-L1023.

The formulated ALS-L1023 capsule was orally given to a male patient who was diagnosed with the exudative age-related macular degeneration three times daily with 2 capsules on each occasion for 12 weeks. Then, the macular area of the patient was photographed, and the size of macular degeneration area was compared with its photograph taken before administration. As shown in FIG. 6, no progression was observed in the macular degeneration area. Thus, ALS-L1023 is expected to be effective in preventing and treating the age-related macular degeneration.

Experimental Example 6—Safety Test of ALS-L1023

Melissa leaf, from which the test substance ALS-L1023 was isolated, has been used as a food or medicine over a long period of time, and classified by US FDA as GRAS (generally regarded as safe). Thus, the test substance ALS-L1023 was considered as non-toxic, and the present experiment was performed as an acute toxicity test (limit test) by a single oral dose at 2000 mg/kg of ALS-L1023 in accordance with the OECD guidelines.

Ten male and ten female rats were randomly divided into the control and experimental groups, each consisting of five animals, respectively. The control groups were administered with 1 ml/150 g (body weight) of corn oil, and the experimental groups were administered with 2000 mg/kg of ALS-L1023 in corn oil. Since the test substance ALS-L1023 was not dissolved in water, it was suspended in corn oil to be used for the test. The test substance was prepared on the day of administration, and suspended by vortexing prior to administration.

First, one rat was orally administered, followed by observation for 24 hrs. Next, two rats were orally administered, followed by observation for 72 hrs. Then, the rest 17 rats were orally administered, and observed for toxicity findings for 30 min. Thereafter, the observations were performed every 30 min for 4 hrs. Subsequently, the observations were performed twice a day for 14 days, and body weight and temperature were recorded every day.

On the last day of the experiment, the rats were euthanized using $CO_2$ and autopsied. Abnormal tissues examined by the pathologist's view were excised, and subjected to histological examination.

As a result, in the case of a single oral dose at 2000 mg/kg of ALS-L1023 into each of the five male and female rats, no significant toxicity findings were observed over the course of the 14 day observation period.

In both control and experimental groups, distinct clinical abnormalities were not observed. However, one female rat became slightly excited at 60 min after administration, but maintained stable at 90 min after administration.

Figure 7:
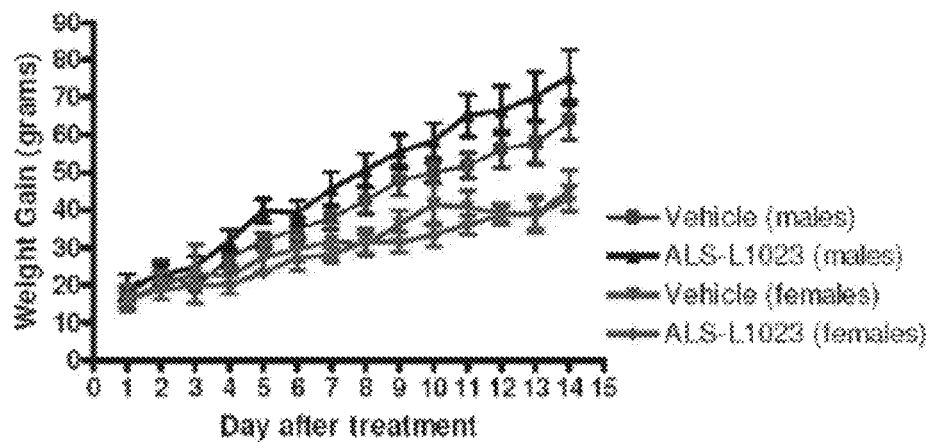
FIG. 7 is a graph showing the changes in rat body weight according to the toxicity test by a single oral dose at 2000 mg/kg of ALS-L1023.
Figure 8:
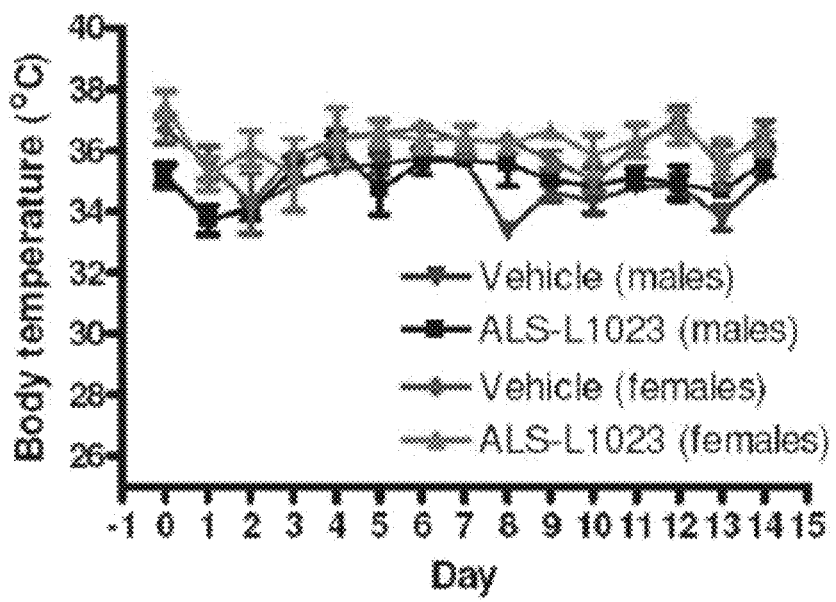
FIG. 8 is a graph showing the changes in rat body temperature according to the toxicity test by a single oral dose at 2000 mg/kg of ALS-L1023.

In addition, ALS-L1023 administration did not affect the body weight and temperature in both control and experimental groups (see FIGS. 7 and 8).

Figure 9:
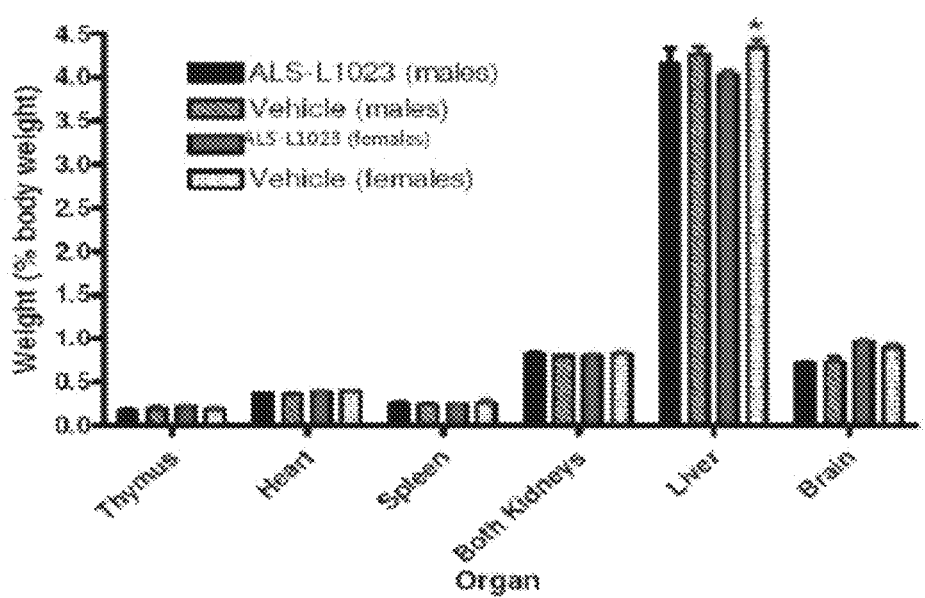
FIG. 9 is a graph showing the relative organ weight values, shown as a percentage of the total body weight according to the toxicity test by a single oral dose at 2000 mg/kg of ALS-L1023.

Relative weights (%) of thymus, heart, spleen, kidney, liver, and brain with respect to the total body weight are shown in FIG. 9. A slight, but statistically significant increase was observed in the liver weight of the female rat in the control group, as compared with that of the female rat administered with ALS-L1023, but not in that of male rats. Abnormal autopsy findings and other peculiar findings were not found.

Moreover, although some abnormal findings were detected by the pathologist's view, histological examination thereof showed no evidence of abnormality.

Consequently, a single oral dose at 2000 mg/kg of ALS-L1023 did not induce any toxic symptoms over the course of the observation period.

An ethyl acetate fraction of *Melissa* leaf of the present invention has strong and excellent anti-angiogenic and MMP inhibitory activities. Therefore, the composition comprising the ethyl acetate fraction of *Melissa* leaf of the present invention can be used as an agent for the treatment or prevention of angiogenesis-related diseases and MMP-mediated diseases.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of reducing neovascular ocular diseases or treating age-related macular degeneration (AMD) in a subject, comprising administering to a subject in need thereof *Melissa* leaf extract, which has been extracted with 75% ethanol, and concentrated, and then the concentrated alcohol extract is suspended in water, and fractionated with ethyl acetate, and dried to obtain the ethyl acetate fraction of *Melissa* leaf.

2. A method of reducing neovascular ocular diseases or treating age-related macular degeneration (AMD) in a subject, comprising (i) extracting *Melissa* leaf with 75% ethanol; (ii) concentrating the alcohol extract; (iii) suspending the concentrated alcohol extract in water; (iv) fractionating the alcohol extract in water with ethyl acetate; (v) drying the ethyl acetate fraction to obtain the ethyl acetate fraction of *Melissa* leaf; and administering to a subject in need thereof the obtained ethyl acetate fraction of *Melissa* leaf.

* * * * *